US00PP09403P

United States Patent [19]

Olij

[11] Patent Number: Plant 9,403

[45] Date of Patent: Dec. 19, 1995

[54] HYBRID TEA ROSE PLANT NAMED 'RUIHUOLY'

[75] Inventor: H. Olij, De Kwakel, Netherlands

[73] Assignee: De Ruiter's Nieuwe Rozen B.V., Netherlands

[21] Appl. No.: 379,271

[22] Filed: Jan. 27, 1995

[51] Int. Cl.[6] ..... A01H 5/00

[52] U.S. Cl. ..... Plt./19

[58] Field of Search ..... Plt./11, 18, 19, Plt./20

*Primary Examiner*—Howard J. Locker

*Attorney, Agent, or Firm*—Christie, Parker & Hale

[57] ABSTRACT

A new variety of Hybrid Tea rose plant having medium pink flowers and suitable for growing under glass.

2 Drawing Sheets

SUMMARY OF THE INVENTION

The present invention relates to a new and distinct variety of rose plant of the Hybrid Tea rose class which was discovered as a naturally occurring mutation in a controlled planting of the variety 'Ruirovingt', U.S. Plant Pat. No. 8,528. The varietal denomination of the new variety is 'Ruihuoly'. The new variety was isolated and asexually reproduced by budding in Holland.

Among the novel characteristics possessed by this new variety which distinguish it from its parent and all other varieties of which I am aware are its attractive medium pink colored flowers of good form borne on a floriferous plant with long stems and suitable for production of cut flowers under glass. The new variety can be reproduced through propagation by cuttings, grafting, budding and micropropagation.

Asexual reproduction by budding of the new variety as performed in Holland shows that the foregoing and other distinguishing characteristics come true to form and are established and transmitted through succeeding propagations.

BRIEF DESCRIPTION OF ILLUSTRATION

The accompanying illustrations show typical specimens of the vegetative growth and flowers of the new variety in different stages of development depicted in color as nearly true as it is reasonably possible to make the same in a color illustration of this character. Colors may vary depending upon growing conditions under different climate, soil, and cultivation conditions, and phenotypic expression may also vary with light, cultural, and environmental conditions.

One of the accompanying illustrations shows cut flower form of the new variety to illustrate optimum flower form and the other illustration shows details of the new rose variety in color more nearly correct for the variety.

DESCRIPTION OF THE NEW VARIETY

The following is a detailed description of the new variety, with color terminology in accordance with the Royal Horticultural Society Colour Chart (RHSCC) and horticultural terminology in accordance with standard terminology used in UPOV-approved horticultural guidelines. The terminology used in color descriptions herein refers to plate numbers in the aforementioned color chart.

Parentage: Mutation of 'Ruirovingt'.

Class: Hybrid Tea.

As can be seen in the accompanying detail illustration there is shown a new shoot, 1; compound three, five and seven leaflet leaves, 2, 3 and 4, respectively a stem, 5; buds, 6 and 7; a flower, 8, about one-third open; and a flower, 9, more fully open. Also shown are flower stems 10, 11 and 12, with reproductive organs displayed. The other illustration shows cut flower form of the new variety.

The following further horticultural description is based on observations made of specimens grown under glass in Holland.

FLOWER

Blooming habit: Nearly continuous; average production about 240 blooms/m$^2$/year.

A. Bud:

(1) *Size.*—Medium, about 3 to 4 cm long and about 2 to 3 cm wide.

(2) *Form.*—Ovate (shape of longitudinal section just before separation of sepals); urn-shaped after sepals part.

(3) *Color.*—As sepals divide, near 66C to 66D.

(4) *Sepals.*—Longer than green bud, generally simple to foliated, upper surface near 139A, under surface near 138C.

(5) *Peduncle.*—Long; Aspect — straight; Strength — erect, very strong. Color — medium green, near 138B to 138C.

B. Bloom:

*Flower.*—Large; viewed from above — irregularly rounded; viewed from side — (a) upper part of fully opened flower, flattened convex; (b) lower part of fully opened flower, flattened convex.

(1) *Size.*—Average size when fully expanded — about 7 to about 8 cm, stem length about 50 cm.

(2) *Borne.*—Singly, one to a stem.

(3) *Form.*—High centered, exhibition type, spiral imbricated, outer petals roll under, some petals quill to points.

(4) *Petalage.*—Fully double, about 26.

(5) *Color.*—When sepals part and petals begin petal top surface appears cream, near 66C and 66D to near 61D; petal undersurface near 66C to 66D. Overall tonality from a distance is medium pink. Color at point of petal attachment, near 4C to 4D upper side and near 7C underside.

(6) *Peduncle.*—Generally smooth.

(7) *Fragrance.*—Weak.

C. Petals:

(1) *Texture.*—Crisp.

(2) *Appearance.*—Inside velvety and outside satiny.

(3) *Form and size.*—Broad, medium, strong undulation of margin.

(4) *Arrangement.*—Regularly arranged, imbricated.
(5) *Petaloids.*—Several.
(6) *Lasting Quality.*—Long-lasting quality on plant and after cutting.

REPRODUCTIVE ORGANS

A. Stamens, filaments and anthers:
*Arrangement and color.*—Regularly arranged around styles; color of filaments — yellow with orange red tips.
B. Pollen:
*Color.*—Near 12A to 12C.
C. Styles: Long, stigma above mouth of receptacle, yellow.
D. Stigmas: Positioned below anthers, near 12C.
E. Hip: Funnel-shaped, medium seed vessel at petal fall.

PLANT

A. Form: Narrow, bushy, average disease resistance, medium height and width.
B. Growth: Vigorous.
C. Foliage: Compound 3, 5 and 7 leaflets.
(1) *Size.*—Medium.
(2) *Quantity.*—Abundant.
(3) *Color.*—Young shoot — medium to strong anthocyanin coloration, green upper surface, bronze to reddish brown with green infusion on undersurface; mature leaf color — near 137A to 139A.
(4) *Shape.*—Broad oval.
(5) *Texture.*—Upper side is leathery and medium glossy; underside is matte.
(6) *Edge.*—Serrate, shallow.
(7) *Serration.*—Ordinary, acuminate apices.
(8) *Leaf stem.*—Color — medium green, near 138B.
(9) *Stipules.*—Long, narrow, medium green, distinct darker green auricle.
(10) *Leaflets.*—Cross section — slight convex; strong undulation at margin; terminal leaflet — blade medium length and broad width, rounded base.
D. Wood:
(1) *New wood.*—Color — young shoots have medium to strong anthocyanin; coloration — reddish brown with green.
(2) *Old wood.*—Color — medium green, near 138B.
E. Prickles (thorns): Present.
*Quantity.*—(Main stalk) — ordinary; On laterals from stalk — ordinary.
*Shape of lower side.*—Concave.
*Length.*—Short with few long prickles.
*Color.*—Near 159A.
*Position.*—Irregular.

What is claimed is:

1. A new and distinct variety of rose plant of the Hybrid Tea rose class, substantially as shown and described.

* * * * *

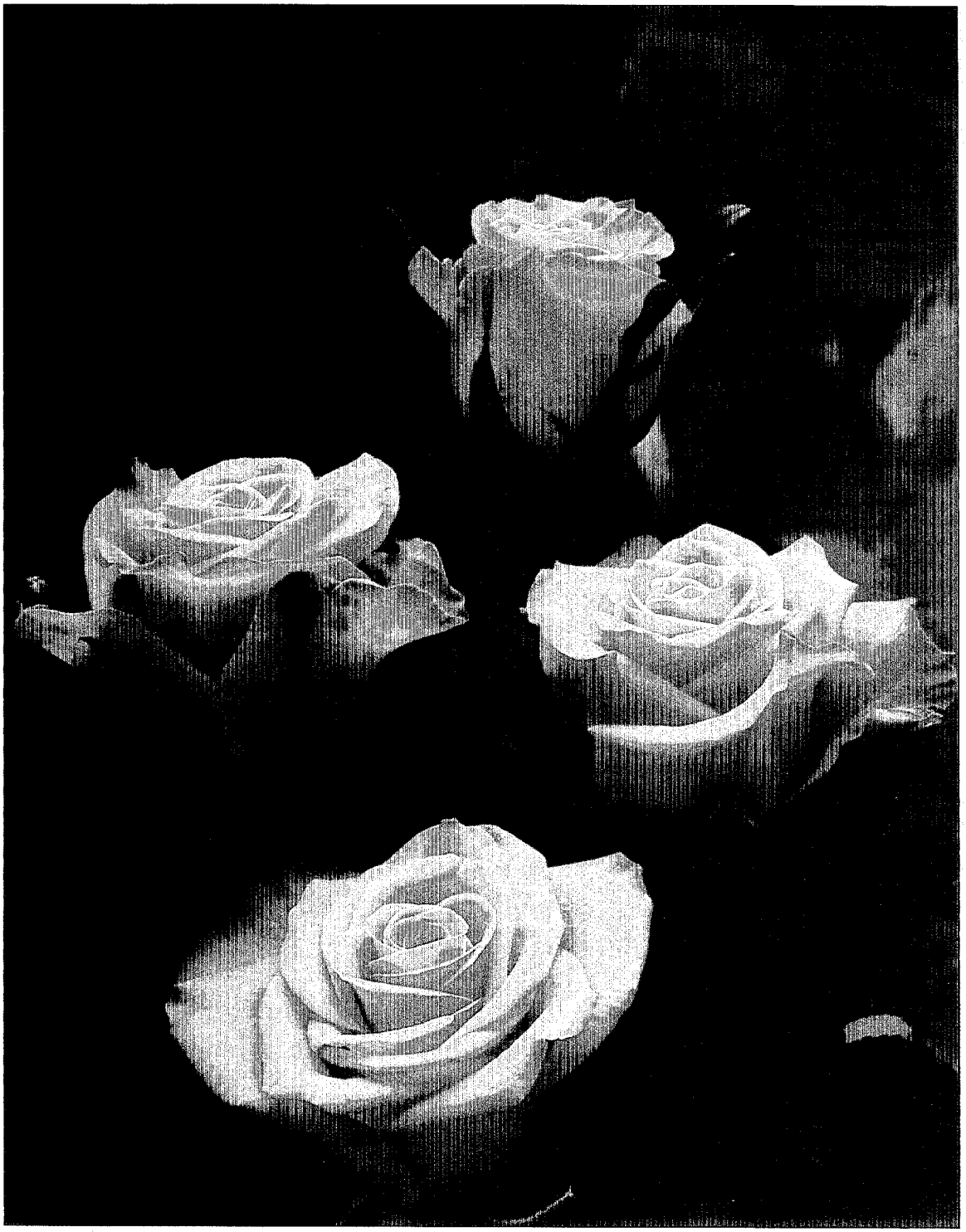

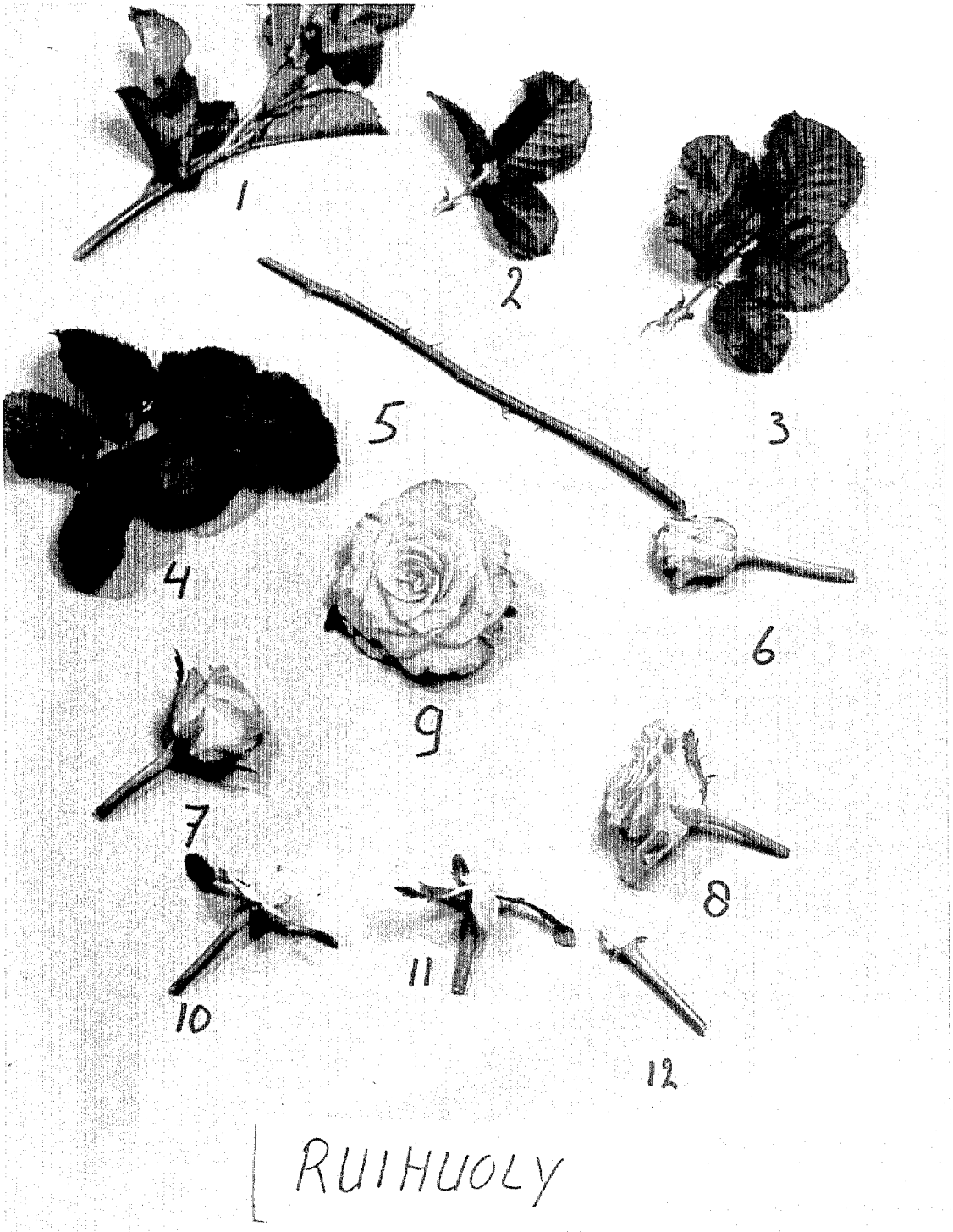
1
2
3
4
5
6
7
8
9
10
11
12
RUIHUOLY